US006958396B2

(12) United States Patent
Bakker

(10) Patent No.: US 6,958,396 B2
(45) Date of Patent: Oct. 25, 2005

(54) 8-{4-[3-(5-FLUORO-1H-INDOL-3-YL)-PROPYL]-PIPERAZIN-1-YL}-2-METHYL-4H-BENZO[1,4]OXAZIN-3-ONE MESYLATE WITH HIGH AFFINITY FOR THE DOPAMINE D2 RECEPTOR AND THE SEROTONIN REUPTAKE SITE

(75) Inventor: Cornelis Bakker, Weesp (NL)

(73) Assignee: Solvay Pharmaceuticals B.V., Weesp (NL)

(*) Notice: Subject to any disclaimer, the term of this patent is extended or adjusted under 35 U.S.C. 154(b) by 0 days.

(21) Appl. No.: 10/432,225

(22) PCT Filed: Feb. 19, 2002

(86) PCT No.: PCT/EP02/01795

§ 371 (c)(1),
(2), (4) Date: May 22, 2003

(87) PCT Pub. No.: WO02/066473

PCT Pub. Date: Aug. 29, 2002

(65) Prior Publication Data

US 2004/0024207 A1 Feb. 5, 2004

(30) Foreign Application Priority Data

Feb. 21, 2001 (EP) .............................................. 01200610

(51) Int. Cl.⁷ ..................... A61K 31/538; C07D 413/14
(52) U.S. Cl. ..................................... 544/105; 514/230.5
(58) Field of Search ........................ 544/105; 514/230.5

(56) References Cited

U.S. PATENT DOCUMENTS

| 5,002,948 | A | 3/1991 | Perregaard et al. |
| 5,242,925 | A | 9/1993 | Boettcher et al. |
| 5,532,241 | A | 7/1996 | Bottcher et al. |
| 5,576,321 | A | 11/1996 | Krushinski, Jr. et al. |
| 5,693,655 | A | 12/1997 | Bottcher et al. |
| 6,214,829 | B1 | 4/2001 | Feenstra et al. |
| 6,251,908 | B1 | 6/2001 | Bottcher et al. |
| 6,262,087 | B1 | 7/2001 | Perregaard et al. |
| 6,314,896 | B1 | 11/2001 | Marin et al. |
| 6,352,988 | B2 | 3/2002 | Perregaard et al. |
| 6,391,896 | B1 | 5/2002 | Van Hes et al. |
| 6,552,044 | B2 | 4/2003 | Perregaard et al. |
| 6,828,325 | B2 | 12/2004 | Feenstra et al. |
| 2001/0020095 | A1 | 9/2001 | Perregaard et al. |
| 2001/0021777 | A1 | 9/2001 | Perregaard et al. |

FOREIGN PATENT DOCUMENTS

| DE | 41 27 849 A1 | 2/1993 |
| DE | 43 33 254 A1 | 4/1995 |
| DE | 44 14 113 A1 | 10/1995 |
| DE | 197 30 989 A1 | 1/1999 |
| EP | 0 376 607 A1 | 7/1990 |
| EP | 0 722 941 A2 | 7/1996 |
| GB | 1075156 | 7/1967 |
| HU | HU 218 935 B | 10/1995 |
| WO | WO 97/17343 | 5/1997 |
| WO | WO 98/28293 | 7/1998 |
| WO | WO 99/03855 | 1/1999 |
| WO | WO 99/05140 | 2/1999 |
| WO | WO 99/67237 | 12/1999 |
| WO | WO 01/14330 A2 * | 3/2001 | ......... C07D/209/00 |
| WO | WO 03/068207 | 8/2003 |

OTHER PUBLICATIONS

Robichaud et al., "Recent Advances in Dopamine $D_3$ and $D_4$ Receptor Modulation," *Ann. Rep. Med. Chem.* 35:11–21 (2000).

Tenbrink et al., "Recent Advances in Dopamine $D_3$ and $D_4$ Receptor Ligands and Pharmacology," *Ann. Rep. Med. Chem.* 29:43–51 (1994).

* cited by examiner

*Primary Examiner*—Johann Richter
*Assistant Examiner*—Chukwuma Nwaonicha
(74) *Attorney, Agent, or Firm*—Finnegan, Henderson, Farabow, Garrett & Dunner, L.L.P.

(57) ABSTRACT

The invention relates to the novel mesylate of a phenylpiperazine derivative of the formula (I). This salt has favorable properties as compared with the free base of this compound.

6 Claims, No Drawings

8-{4-[3-(5-FLUORO-1H-INDOL-3-YL)-PROPYL]-PIPERAZIN-1-YL}-2-METHYL-4H-BENZO[1,4]OXAZIN-3-ONE MESYLATE WITH HIGH AFFINITY FOR THE DOPAMINE D2 RECEPTOR AND THE SEROTONIN REUPTAKE SITE

The invention relates to the novel phenylpiperazine derivative of the formula (I):

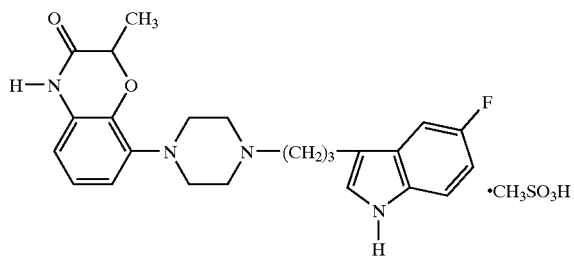

International Publication No. WO 01/14330 A2 relates to a group of novel phenyl piperazines. The compounds of that group show high affinity for both the dopamine $D_2$ receptor and the serotonin reuptake site. This combination is useful for the treatment of schizophrenia and other psychotic disorders which enables a morecomplete treatment of all disease symptoms (e.g. positive symptoms and negative symptoms).

The compounds show activity as antagonists at dopamine $D_2$ receptors as they potentially antagonize apomorphine-induced climbing behaviour in mice. The compounds also show activity as inhibitors of serotonin reuptake, as they potentiate 5-HTP induced behaviour in mice.

The compounds are active in therapeutic models sensitive to clinically relevant antipsychotics (e.g. the conditioned avoidance response; Van der Heyden & Bradford, Behav. Brain Res., 1988, 31:61–67) and antidepressants or anxiolytics (e.g. suppression of stress-induced vocalization; van der Poel et al., Psychopharmacology, 1989, 97: 147–148).

In contrast to clinically relevant dopamine $D_2$ receptor antagonists the described compounds have a low propensity to induce catalepsy in rodents and as such are likely to induce less extrapyramidal side effects than existing antipsychotic agents.

The inhibitory activity of serotonin reuptake inherent in these compounds may be responsible for the therapeutic effects observed in behavioural models sensitive to either antidepressants or anxiolytics.

The compounds can be used for the treatment of affections or diseases of the central nervous system caused by disturbances in either the dopaminergic or serotonergic systems, for example: aggression, anxiety disorders, autism, vertigo, depression, disturbances of cognition or memory, Parkinson's disease, and in particular schizophrenia and other psychotic disorders.

It has now been found that the mesylate of the above formula has particularly favorable properties in comparison with the free base (i.e. compound no. 89 of International Publication No. WO 01/14330 A2).

This mesylate compound is much better soluable in water than the free base resulting in a good bio-availability.

The compound has a centre of chirality; both the racemic mixture and the individual enantiomers belong to the invention.

The compound can be brought into forms suitable for administration by means of suitable processes using auxiliary substances such as liquid and solid carrier materials.

The free base of compounds in general can be prepared as described in International Publication No. WO 01/14330 A2. The compounds of the present invention can be prepared by reaction of a compound of the formula

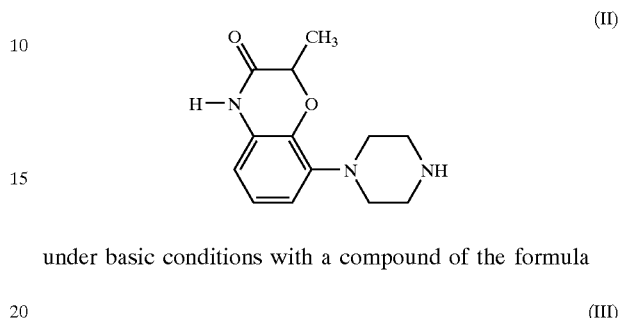

under basic conditions with a compound of the formula

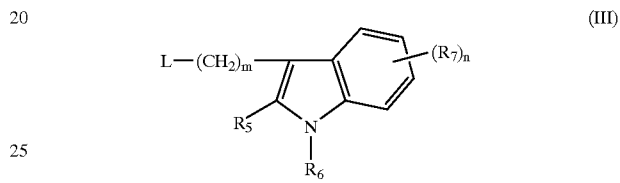

in which L is a leaving group such as a halogen atom or a mesylate group, m is 3. $R_5$ and $R_6$ are both hydrogen, and $R_7$ is a fluorine on the 5-position of the indole ring while n is 1.

For example, a mixture of the piperazine of formula (II) (3.36 g, 13.6 mmol), the 5-fluoro indole-mesylate of formula (III) (4.1 g, 15.1 mmol), triethylamine (2 ml) and a catalytic amount of KI in $CH_3CN$ (100 ml) was heated under reflux for 18 hours after which the reaction mixture was concentrated in vacuo and purified by chromatography ($SiO_2$, dichloromethane/methanol/ammonium hydroxide =92/7.5/0.5).

Yield of the free base of the compound was 58%, $[\alpha]_D^{25}=-24°$ (methanol).

One enantiomer of the starting compound of formula (II) can be prepared according to the following scheme:

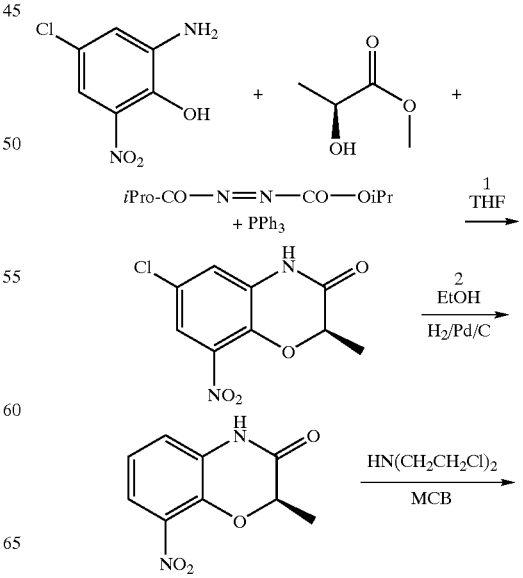

-continued

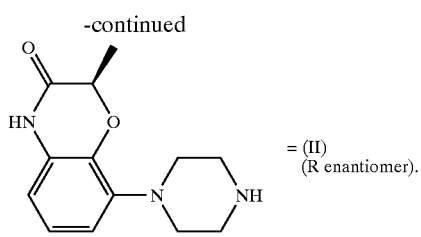

= (II)
(R enantiomer).

EXAMPLE 2.0 g (4.7 mmol) of the free base obtainable as described in International Publication No. WO 01/14330 A2 (compound no. 89) is suspended in 40 ml of methanol. The suspension is warmed to 60° C., and a solution of 0.45 g (4.7 mmol) of methanesulfonic acid in 10 ml of methanol is added in about two minutes. A clear solution is obtained. After stirring for 5 minutes at 60° C. the crystallization begins. The solution is cooled slowly in 60 minutes to 20° C., and stirred at that temperature for 30 minutes. Further cooling to 0° C. in 60 minutes and stirring for 90 minutes is carried out. The solid material is isolated by means of filtration, washed with 5 ml of methanol and dried during a night at 50° C. under reduced pressure. Yield 2.17 g (88%) of white coloured mesylate.

What is claimed is:

1. A compound of formula:

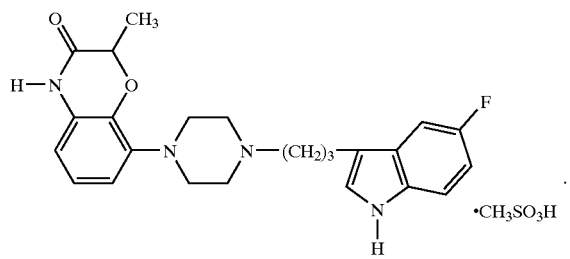

2. A pharmaceutical composition for treating one or more central nervous system disorders in a patient in need thereof, comprising at least one compound of claim 1 in a therapeutically effective amount, and at least one auxiliary substance.

3. A method of treating a patient suffering from one or more disorder of the central nervous system, comprising administering a therapeutically effective amount of at least one compound of claim 1 to the patient.

4. The method of claim 3, wherein the one or more disorder of the central nervous system is chosen from aggression, anxiety disorders, autism, vertigo, depression, disturbances of cognition, disturbances of memory, Parkinson's disease, and psychotic disorders.

5. The method of claim 4, wherein the psychotic disorder comprises schizophrenia.

6. A pharmaceutical composition comprising at least one compound of formula:

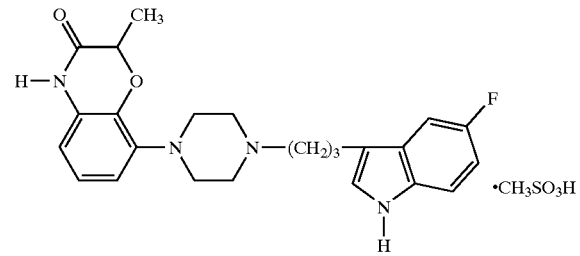

and at least one auxiliary substance.

* * * * *